United States Patent [19]
Morris

[11] Patent Number: 5,976,132
[45] Date of Patent: Nov. 2, 1999

[54] BIPOLAR SURGICAL SHEARS

[76] Inventor: James R. Morris, 1120 Cathedral Rock, Sedalia, Colo. 80135

[21] Appl. No.: 08/958,202

[22] Filed: Oct. 10, 1997

[51] Int. Cl.⁶ .................................................. A61B 17/36
[52] U.S. Cl. ................... 606/49; 606/41; 606/50; 606/52; 128/DIG. 28
[58] Field of Search ............... 606/41–52; 128/897–899, 128/DIG. 22

[56] References Cited

U.S. PATENT DOCUMENTS

| | | | |
|---|---|---|---|
| 5,116,332 | 5/1992 | Lottick | 606/42 |
| 5,324,289 | 6/1994 | Eggers | 606/49 |
| 5,352,222 | 10/1994 | Rydell . | |
| 5,540,685 | 7/1996 | Parins et al. . | |
| 5,573,534 | 11/1996 | Stone . | |
| 5,658,281 | 8/1997 | Heard . | |
| 5,779,701 | 7/1998 | McBrayer et al. | 606/46 |

FOREIGN PATENT DOCUMENTS

WO 96/27338  9/1996  WIPO .

*Primary Examiner*—Cary O'Connor
*Assistant Examiner*—Michael Astorino

[57] ABSTRACT

In a bipolar surgical shears, pivoted cutting members serve as a first electrode, and separate conductors, mounted on the cutting members and insulated therefrom, serve as second and third electrodes. One of the second and third electrodes is connected to a terminal on the opposite cutting member through a pivot pin comprising an insulating tube, so that all power supply connections are mounted on one of the pivoted cutting members. A power supply can be switched selectably to a selected one, or both, of the second and third electrodes.

10 Claims, 2 Drawing Sheets

BIPOLAR SURGICAL SHEARS

BACKGROUND OF THE INVENTION

1. Field of the Invention

The present invention relates to surgical shears for cutting through tissue in the course of an operation. More specifically, the invention relates to such shears that are provided with a high frequency voltage across electrical alternative electrodes to create current in adjacent tissue causing hemostasis of tissue around the cut made by the shears. More specifically, the invention relates to multiple electrodes permitting selective switching to more specifically locate the hemostasis to a position which the surgeon wishes to control.

2. Description of the Related Art

The concept of using bipolar electrodes in connection with surgical instruments has been employed in various ways in prior art. Hemostasis created in tissue adjacent the instrument helps control bleeding in the area in which surgery is being performed so that the surgeon's view is less obstructed by blood. Any improved visability in the region of his work will help the surgeon. Nevertheless, there is sometimes a problem of accumulation of fluid, coagulants and tissue on the instrument in the course of surgery which is obstructing and may waste time to clear away. Furthermore, even though hemostasis has been confined somewhat more specifically to the region of surgery by bipolar instruments, the region of hemostasis cannot be as specifically controlled as a surgeon might wish. For example bleeding from one side of the sheared tissue may not be as controllable as from the other side, and until now there has been no means of selectively controlling on which side of the cut hemostasis can be made to occur or at least made dominant.

BRIEF SUMMARY OF THE INVENTION

The present invention has application to medical instrumentation generally, not only to surgical shears, in that it provides for the first time the concept of embedded electrodes. In accordance with the invention, the electrode of a bipolar instrument will have a minimal surface area exposed so that fluids and coagulated fluids and tissue do not tend to accumulate on the electrode surface, and to the limited extent they may, there is less accumulation to obstruct the view of the surgeon. The concept may be accomplished by coating with biocompatable insulation all of the instrument except active or potentially active areas providing electrodes. Insulating materials which do not adversely affect the tissue on which it is being used, and preferably reject accumulations of blood, coagulants and tissue, are preferably employed. Electrodes and their associated conductors for connecting them ultimately to a power supply may then be mounted on the instrument on the insulated coating. Mounting may be done either using bonding properties of the insulation as an adhesive, or more commonly by using a separate adhesive, such as epoxy glue, to mount the electrodes and their conductors on the coated instrument, thus maintaining insulation between the electrode and the instrument's conductive base metals. Further coating is then applied over the conductor and the electrode except for those selected active areas which are critical to the functioning of the electrode. Active areas are minimized in exposed area within limits of effectiveness of the electrode in use. The area which is exposed must be kept at a sufficiently close spacing for the electrode with which it cooperates to be effective when moist tissue is interposed between the electrodes.

The concept of an embedded electrode may be used in all sorts of instrumentation, including scalpels and forceps. Of course a preferred application is in surgical shears, placing the exposed part of the embedded electrode somewhere near and along the cutting edge. On the other hand, the concept is useful on various types of medical instrumentation where voltage needs to be applied and where minimum electrode area will serve to minimize accumulation of fluids, coagulants, and tissue. In the surgical shears application the electrodes are embedded except for a very narrow edge which is spaced from and along a conductive shearing surface but sufficiently proximate thereto, so that when moist tissue is contacted by both electrodes hemostatic current will flow through the tissue. Current must flow through the tissue in which the surgeon wishes to produce a hemostasis.

The embodiment of the embedded conductor and electrode shown and described herein relates to novel surgical shears wherein the surgical shears themselves, or at least the shearing portions of shears, are metallic or otherwise conductive. The exposed edge of an embedded electrode is placed near but spaced from the conductive shearing surfaces. Across shearing surfaces and the embedded electrode as cooperating bipolar electrodes a high frequency voltage is applied to produce current through tissue contacted by both electrodes to create hemostasis. In preferred embodiments of the invention, a separate embedded electrode is carried on the blade portion of each of the two members of the shears with the electrode supported proximate to the shearing surface. Each of the electrodes is electrically isolated from the other by the insulating and embedding coating. While embedding is not essential to the operativeness, it is desirable as discussed above. Conductors for the respective embedded electrodes permitting connection to the power source are also preferably supported and embedded on the respective shear members.

An important aspect of the present invention is that despite the location of electrodes on each of the separate members, terminals connected to each of the electrodes are located and mechanically supported on only one of the shear members. Thus the complication in the prior art of electrical connections to both members is avoided. Those connections and the conductors to them are best located at one place on one member out of the surgeon's way. In accordance with the present invention, the embedded electrode supported on one of the blade members has a connecting conductor extending through an insulating pivotal connection to a further embedded conductor joining the member to a terminal on the other member. With three (or more) terminals for the electrodes on one shear member, the terminals can be grouped together and, if desired, connected to a common plug connector for the respective connections to the power supply.

In accordance with the present invention, a switching means is provided which allows selective connection to different pairs of electrodes. The base metal of the shears preferably provides a common electrode which advantageously may be connected to one terminal of a high frequency power supply. Either or both of the embedded electrodes supported on respective shear members may be connected through separate switches to the other terminal of the power supply, thereby providing selectable power to a switch selected electrode. The power supply provides a generally constant voltage at a selected frequency between 250 kilohertz and 2 megahertz in order to generate current through the tissue. The tissue is contacted by two bipolar active electrodes, and the resulting current through the tissue is effective to produce hemostasis in that tissue. In this way, the surgeon may select which side of the shears, and therefore which side of the tissue being cut, will be most actively affected by the current producing hemostasis. If desired, he may select the use of both electrodes. He may also select in a given situation not to use the electrodes and thus not produce hemostasis. The material of the insulating coating may be selected so that such blood, other fluids, coagulants and tissue do not attach to it, or at least attach to a minimal degree. The shearing surfaces of the shears are in effect self-cleaning so that material which might tend to accumulate on them is wiped away in use. The contact between the conductive shearing surfaces puts both members at the same potential, even though the connection pivot point is insulating. Therefore, both shearing surfaces are part of a common electrode, but the control and location of the area of hemostasis depends upon placement of the embedded electrodes, so that the designer in an individual case may place these embedded electrodes in positions found to be most effective, and allow them to extend along a shearing surface for distances found to be most effective.

It should be observed that a bipolar arrangement is not essential to the invention. For example, in a monopolar system, the shearing surfaces of the blades may be connected to the ground of the monopolar system and the electrodes preferably to the same elevated high frequency potential through their respective switch members.

More specifically, the present invention relates to a surgical instrument having electrodes across which a high-frequency, constant voltage signal may be applied to generate currents through tissue producing hemostasis. At least one electrode is supported on a conductive portion of the surgical instrument embedded in an insulating coating which insulates the electrode from the base metal of the instrument. Preferably only an edge of the electrode is exposed proximate to any exposed metallic surface of the instrument providing the other electrode. Currents may be generated between the electrodes through moist tissue upon contact with that tissue by the electrodes when suitable high frequency constant voltage is applied between electrodes.

A specific surgical instrument in accordance with the present invention is surgical shears which include high-frequency electrodes for selectively cauterizing areas being cut by the shears. The shears are comprised of first and second electrically conductive shear members, each having shearing surfaces and adjacent cutting edges, and having an electrical insulating coating applied to surfaces other than the shearing surfaces. Mechanical fastening means for relatively rotatably connecting together and allowing relative scissors-like motion between the first and second shear members is provided. In operative positions at least part of the shearing surfaces are opposed to one another and will be mechanically and electrically in contact with one another during use. Electrode means is supported on each of the shear members and positioned to contact tissue when being cut by the shears. Each electrode means is insulated from the conductive portions of the shear member on which it is supported by the electrically insulating coating. A first electrical conductor supported on and insulated from the first supporting shear member connects a first electrode to terminal means for, in turn, connecting to the power supply. A third electrical conductor is supported on and insulated from the second shear member. It is connected to the electrode means on the second shearing member and connected to electrical connection means passing through the mechanical fastening means rotatably connecting the shear means. A second electrical connector is mechanically supported on and electrically insulated from the first shear member by the insulating coating. The second electrical connection is connected between the electrical connection means passing through the mechanical fastener means and a terminal means for connection to a power supply.

In another aspect the present invention relates to a system for selectively applying high frequency current to tissue being cut by surgical shears to one side, or the other, or both sides of the shears as cutting proceeds. The system uses a high frequency voltage generator and surgical shears comprising at least a pair of interconnected movable blades. The shears have mutually engaging shearing surfaces which provide a common electrode connected to one terminal of said generator. Insulation covers the opposite side of the blades from the shearing surfaces. Electrodes are mounted on insulation on the blades, each electrode having an edge closely spaced from the cutting edge of the shearing surface of the blade on which it is mounted and extending along that edge. Electrical connections from the electrodes supported on each of the blades through separate switches to the other terminal of the generator. By selectively opening and closing switches, one or the other, or both of the mounted electrodes have high frequency voltage applied across that electrode and the shearing surface electrode to produce current in tissue being cut sufficient to generate local hemostasis. The selection of the switches by the surgeon allows the surgeon to produce areas of hemostasis towards one side or the other of the cut, or on both sides thereof.

The present invention also provides a method of preforming surgery using surgical shears in which the base metal of the blades provides the shearing surfaces as one electrode connected to one terminal of a high frequency generator and separate electrodes mounted on each of the blades are insulated from but extend into close proximity with the shearing surfaces over a substantial length of the cutting edge of the shearing surface on each of the blades. Each of the electrodes is connected by separate conductors through separate switches to the other terminal of the high frequency generator. As the shears cut through tissue, the surgeon in separate sequential steps may selectively close one, or the other, or both switches, or leave the switches open, in accordance with his determination of need to cause high frequency current to pass through the tissue between the shearing surfaces and the selected electrode on one side, or the other, or both sides of the cut being made, to produce hemostasis of the tissue in areas thus selected.

The present invention also provides a method of using the surgical shears defined above by producing hemostasis in selected tissue being cut by surgical shears by the following steps. One electrode is connected to one switch of a first terminal of a high frequency generator. The second electrode is connected through another switch to the same terminal of the power supply. The base metal is connected to he other terminal of the power supply. Then the switches are selectively closed to produce current on that side of the cut where it needed by activating a switch for the electrode on that side of the shears.

BRIEF DESCRIPTION OF THE SEVERAL VIEWS OF THE DRAWINGS

For better understanding of the present invention, references made to the accompanying drawings in which.

DETAILED DESCRIPTION OF THE INVENTION

Figure 1:
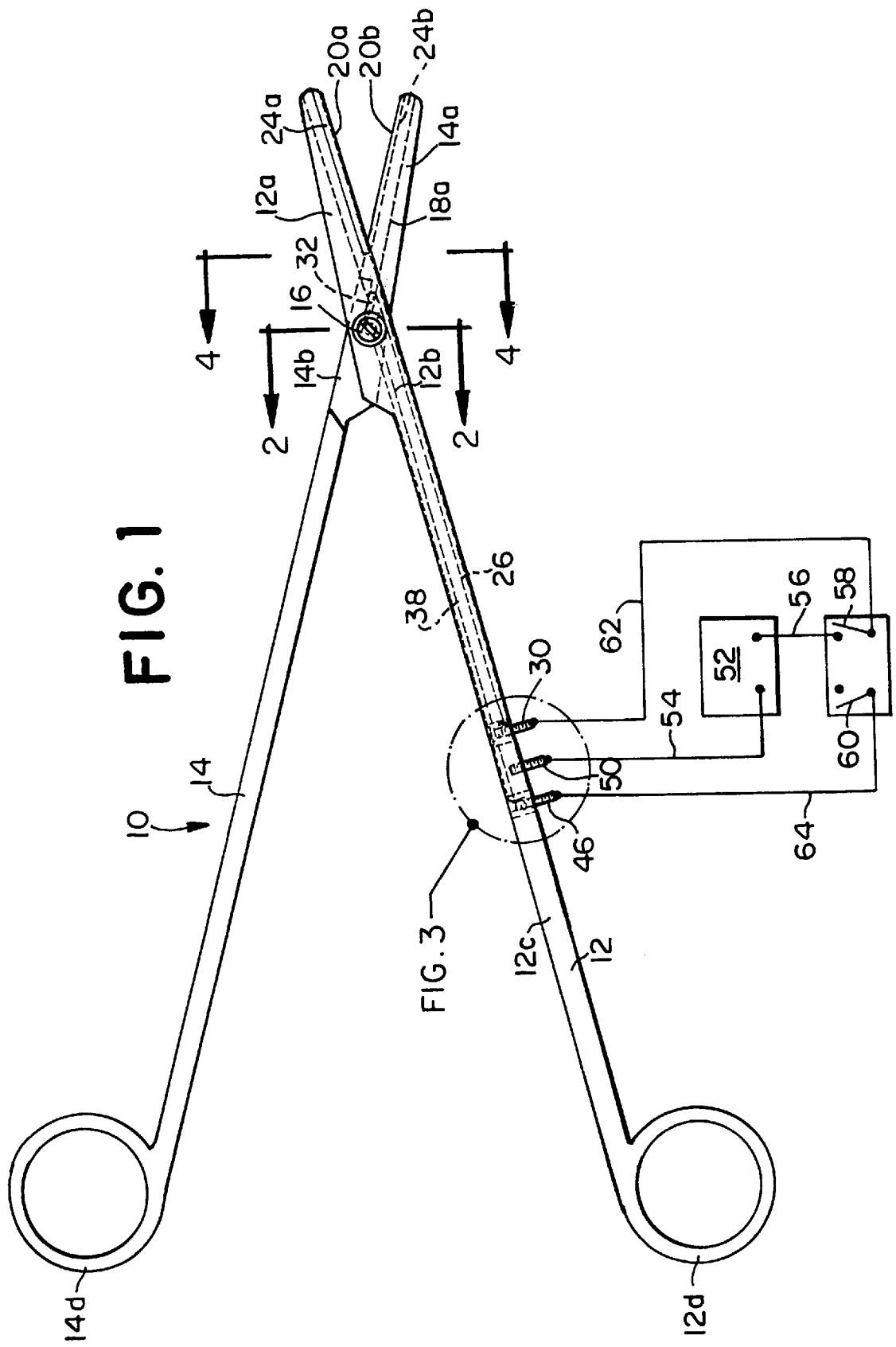
FIG. 1 is a plan view from above showing a preferred embodiment of surgical shears employing the invention, plus the electrical connections thereto shown schematically.

Referring to FIG. 1, a pair of surgical shears, generally designated 10, in accordance with the present invention is illustrated. The shears are made up of relatively conventional first and second shear members 12 and 14 rotatably connected together by connection means 16 permitting relative rotation of members 12 an 14 in scissors-like action. Shear members are composed of blade portions 12a and 14a which continue into the connection regions 12b and 14b respectively. Part of the shear members provide lever arms 12c and 14c which terminate in thumb or finger rings 12d and 14d. Shear members 12 and 14 are typically one piece forged steel members of a formulation that facilitates forging and produces blades which may be sharpened like conventional shears or scissors and preferably retain a sharp edge capable of an extended period of use. The steel should also be capable of carrying high frequency electric currents at essentially constant relatively low voltage. The structure of the surgical shears is intended to be conventional except or the pivotal connection of the shear memers. Just as surgical shears may take a varying form for specialized purposes, shears to which the present invention applies may take any of the varying forms of surgical shears presently in use or any new forms which surgical shears may take in the future. They preferably depart from the conventional in appropriate instances to provide recessed channels or groves conforming to the electrode and conductor members supported on the respective shear members in many embodiments of the present invention. In such event, for example, when the electrodes and conductors are fixed in place and the final insulating coating applied, the overall appearance of the shears remains essentially like shears of the prior art on which electrodes and conductors have not been used.

Figure 4:
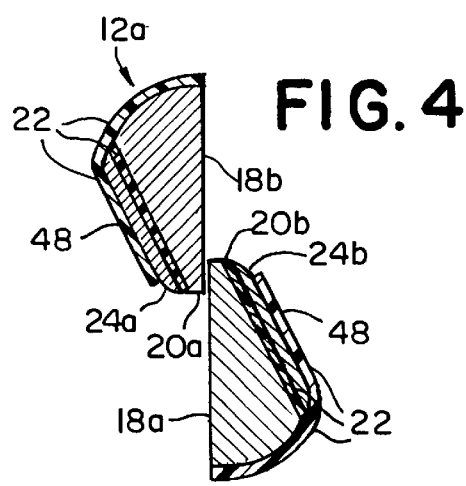
FIG. 4 is a sectional view taken along lines 4—4 of FIG. 1.

As seen in FIG. 4 blades 12a and 14a provide opposed shearing surfaces 18a and 18b. The shearing surfaces are essentially flat and in rubbing contact with one another to facilitate cutting of tissue at the cutting edges at the shearing surfaces where they intersect with the respective faces 20a and 20b as portions of those edges pass each other in the process of cutting tissue with the shears. In FIG. 1 only the shearing surface 18a is visible. Shearing surface 18b is the underside of blade 12a in that view. To assure that the shearing surfaces 18a and 18b in FIG. 4 are self-cleaning, the surfaces shown separated for clarity, are actually in rubbing contact. The rubbing uninsulated surfaces continue to the region of connection 12b and 14b, which are also left uncoated to provide for better action with less friction as the shears are opened and closed about pivoted connection 16. Preferably and advantageously all the rest of the exposed surfaces of both shear members 12 and 14 are coated with an insulating coating such as phenolic resin or other insulating material tending to reject collection of blood, coagulants and tissue. This insulating coating 22 covers the opposite sides of the blade from its connection into the extension region of each shear member 12 and 14. Sheet metal electrodes 24a and 24b respectively, may be adhered by the adhesiveness of the coating. However, in most cases it is preferable to allow the insulating coating 22 to dry before applying an epoxy or other suitable adhesive over the insulating coating and on the electrode surfaces facing the blades and positioning the respective electrodes 24a and 24b on the blades. The insulation should also be selected with suitable dielectric strength to avoid breaking down under the relatively small electrical potentials to be applied between the electrodes and the shearing surfaces.

Figure 3:
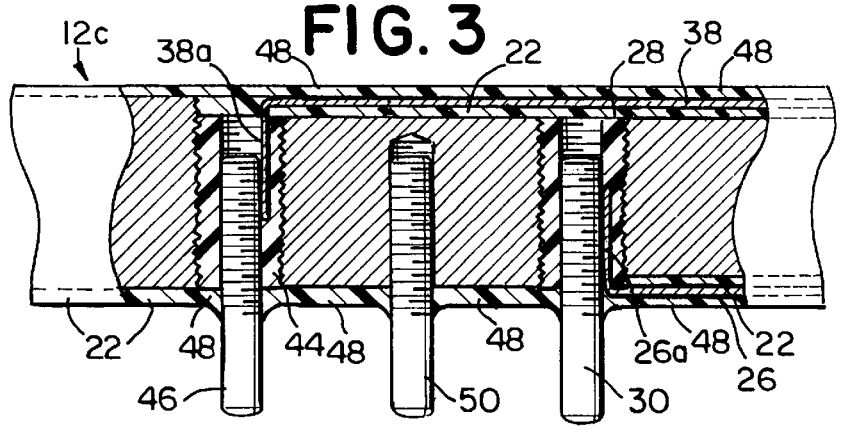
FIG. 3 is a detailed transverse section of the portion of FIG. 1 taken through the region within the dashed circle labeled FIG. 3.

Each of the electrodes and the conductors extending from them back to a terminal may be formed in whole, or in part, of titanium sheet metal which conforms to the surface to which it is adhered. As suggested above, the shear means surface may have been specially configured during forging to accept the electrodes and conductors. For example, electrode 24a may be formed integrally with conductor 26. As seen in FIG. 3 conductor 26, in turn, is preferably terminated in an integral tab 26a bent to fit down into a tubular threaded insulating insert 28. The cylindrical outer surface of the tubular insert 28 may also be threaded to conform to threads in a receiving bore of arm 12c in shear member 12. A rod terminal 30 is preferably threaded at one end to engage threads on the interior surface of insert 28. Upon being screwed into place the threads on terminal 30 deform tab 26a and make good electrical contact, thus providing a terminal 30 for electrode 24a insulated from the base metal of the handle 12c of shear member 12.

Figure 2:
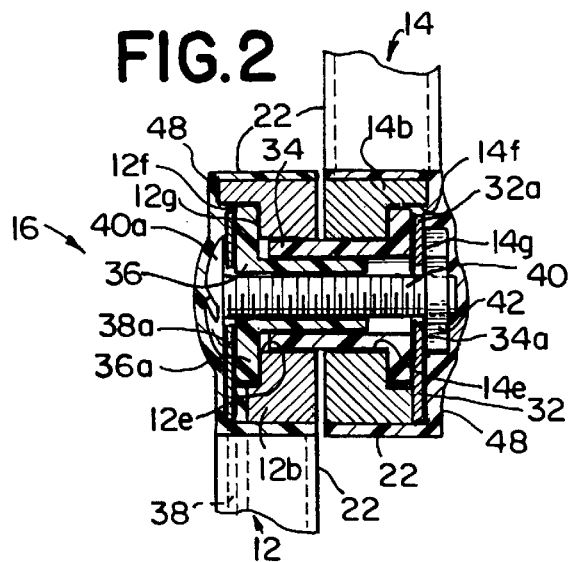
FIG. 2 is a sectional view taken along line 2—2 of FIG. 1.

Titanium sheet metal electrode 24b also is connected to a conductor, preferably an integral sheet titanium piece 32 terminating in a ring portion 32a, as seen in FIG. 2, coaxial with the holes 14c and 12c through the shear members 12 and 14, through which the connecting member 16 passes. Aligned cylindrical bores 14e and 12e of the same diameter pass through shearing members 14 and 12. At the outside surfaces of connecting portions 14b and 12b coaxial counterbore portions 14f and 12f have wider diameters to form planer shoulders 14g and 12g, respectively, between the bore diameters. Interfitting cylindrical bushings 34 and 36 of Delrin, or other suitable moldable resinous insulation material, in turn, fit within the bores. Shoulders 14a and 12a support radially extending flanges 34a and 34b of the bushings 34 and 36 in position. The insulating flange 34a supports the ring 32a terminating titanium sheet conductor 32. The flange 36a supports a similar terminating ring 38a of titanium sheet conductor 38 on the opposite side of the connection structure 16. Conductor 38 is supported on insulation 22 covering the blade of shear member 12, preferably in a preformed groove. A conductive screw 40 provides the connective conductive connection thorough the interfitting bushings 34 and 36 and extending between and beyond the respective terminating rings. The head 40a of the screw 40 enables good electrical contact with the ring 38a of the conductor 38 by engaging ring 38a between them as the flange 34a seat against the bushing 34. As conductive nut 42 is tightened on screw 40 it makes good electrical contact with terminal ring 32a of the conductor 34 and seats against the flange 34a. Of course, the nut and screw hold the shear members 12 and 14 together through the insulating members and enable relative rotatable action between the shear members. Finally as seen in FIG. 3 conductor 38 has an integral tab 38a which is bent to extend inwardly within bushing 44. Bushing 44, like bushing 28, is held in a bore through base metal of the shear member at handle 12c. Insulating bushing 44 may be threaded on it's outside to engage threads in the bore, or is otherwise secured in place. Internal threads in bushing engage threads of the conductive rod terminal 46. As rod 46 is screwed in place its threads engage and deform tab 38 of conductor 38, thus completing a good electrical connection from terminal 46 to electrode 24a through the screw 40 and conductor 32.

It is not only for aesthetic reasons that a further conductive layer 48 needs to be applied over the conductors to provide a smooth surface, but the proper selection of insulating material inhibits collection of biological waste material that otherwise would clutter and obscure the view of the surgeon. The electrodes need not be embeddeed to function, but in accordance with the invention, all but the effective edge proximate to a cooperating shearing surface is preferably coated. The area left exposed at optimum is only that area which is needed to support current at an effective level through the tissue. Designers of individual instruments may determine the required minimum area from the parameters of their particular generator and the properties of the electrodes and conductive materials used. In the case of the electrodes 24a and 24b, the part of the electrode exposed parallels the shearing surface since only part of the exposed part of the electrode is effective at any time as the shears open and close. In accordance with the invention, the area of the electrode surface exposed is consistent with what is the minimum needed to produce reliable current flow through the tissue. That area can be determined experimentally or calculated. Minimizing the area is desirable because by keeping the actual exposed area as small as possible, accumulation of tissue, fluids and coagulants is minimized. In fact, it is an important discovery that by keeping an electrode surface small and embedding the electrode except for a minimum area near the other cutting area, it is possible to minimize the accumulations as previously stated.

Finally, a base metal terminal 50 similar to the others is threaded into a bore into base metal of handle portion 12c. Terminal 50 is located between the terminals 30 and 46 but it will be understood that the relative positions of the terminal is not critical. However, using rod terminals, which may be formed as plug prongs, placing the terminals close together in some form of pattern allows the terminals to be engaged by a plug (not shown) connecting the terminals to separate conductors in a cable, in turn, connecting the separate electrodes back to the power source. It will also be observed that after all of the terminals are in position, additional insulating coating 48 needs to be applied around each terminal as well as on the conductors and electrodes on the shear members. Such added coating embeds the electrode except for its exposed effective area.

It will be understood by those skilled in the art, as diagramed in FIG. 1 that high frequency in a range on the order of 250 kilohertz to 2 megahertz, for example, at constant voltage may be provided by a standard commercially available electrosurgical generator 52. Such an electrosurgical generator such as Force 2 can be procured off the shelf from Pfiger, Valley Lab, and other suppliers. In a preferred arrangement conductor 54 connects one terminal of the power supply 52 to shear member base metal terminal 50, thus applying one potential level to the shearing surface 18b. Uncoated shearing surface 18b, in turn, by its conductive contact to the other shearing surface 18a places both shearing surfaces at the potential applied to terminal 50. The potential difference across the terminals of the generator 52 may be selectively supplied to terminals 30 and 46 by switch means. Conductor 56 is connected from the other pole of the power supply to one pole of each of the switches 58 and 60, here shown in open, nonconducting position. The other sides of the switches are connected, respectively, to terminals 30 and 46 by conductors 62 and 64. Closing switch 58 puts potential on terminal 30 and hence on electrode 24a. Closing switch 60 puts the same potential on terminal 46 and hence electrode 24b. In the embodiment shown in FIG. 4 the potential is applied between the cutting edge of each blade 20a or 20b as well as shearing surfaces 18b and 18a and the respective electrodes 24b and 24a. Thus, by selectively operating the switches the surgeon can have one blade effectively cauterizing on the side where it is needed without the other side being so much affected by the hemostasis. The reverse side is made more effective by selecting the other electrode combination. Alternatively both electrodes may be used simultaneously as the surgeon wishes. Of course, neither may be used if the surgeon does not wish to produce hemostasis.

It will be understood by those skilled in the art the many variations on the structures shown and described will occur to those skilled in the art. All such variations within the scope and spirit of claims are intended to be within the scope of the present invention.

I claim:

1. Surgical shears including high frequency electrodes for selectively cauterizing areas being cut by the shears comprising:

first and second electrically conductive shear members each having shearing surfaces and adjacent cutting edges and having an electrically insulating coating applied to surfaces other than the shearing surfaces;

mechanical fastening means for relatively rotatable connecting together and allowing relative scissor like motion between the first and second shear members so that in operative positions at least part of the shearing surfaces are opposed to one another and will be mechanically and electrically in contact with one another during use;

an electrode supported on each of the shear members in position to contact tissue when being cut by the shears, said electrode being insulated from the conductive portion of the respective first and second members by the electrically insulating coating;

a first electrical conductor supported on and insulated from the first shear member, connected to the electrode on the first shear member and providing terminal means for the connection to a power supply;

a third electrical conductor supported on and insulated from the second shear member and connected to the electrode on the second shear member and connected to electrical connection means passing through the mechanical fastening means, and;

a second electrical conductor mechanically supported on and electrically insulated from the first shear member and insulated from the first electrical conductor and the shearing surface by the insulating coating connected between a terminal means for connection to a power supply and the electrical connection means passing through the mechanical fastener means completing electrical connection to the electrode on the second shear means;

in which the mechanical fastening means for connecting together the shear members include a tubular molded resinous bushing about which the shear members rotate and through which passes a connecting conductor connecting together the third and second electrical conductors.

2. The surgical shears of claim 1, in which the connecting conductor is a part of the mechanical fastening means, and holds together the shear members.

3. The surgical shears of claim 2, in which the tubular molded bushing has a flange at one end, the flange resting against a part of one of the first and second shear members and further including a tubular member with a flange resting against a part of the other of the first and second shear members, the flanges being positioned so that the parts of the shear members against which they rest are located between them, and in which the connecting conductor has radially extending members at opposite ends, the radially extending members being positioned so that said flanges and said parts of the shear members are located between the radially extending members, the radially extending members holding the flanges in place against the respective shear members and holding the shear members in contact with one another.

4. The surgical shears of claim 3, in which said parts of the shear members have aligned bores which receive the tubular members, and in which the aligned bores have outer ends which are counterbored with larger bores, to provide shoulders adjacent said outer ends the larger bores receiving the respective flanges of said bushing and said tubular member, and the flanges resting against the respective shoulders, so that the mechanical fastening means is at least partially within the bores.

5. The surgical shears of claim 4, in which said radially extending members are conductive, and in which the second and third conductors have conductive ends which lie respectively between the radially extending conductive members and the flanges, bear against the respective radially extending conducting members and the respective flanges, and assure good contact and connection between the second and third conductors.

6. The surgical shears of claim 5, in which the connecting conductor is a conductive bolt and the radially extending members at opposite ends of the connecting conductor are a head of the bolt, which rests on one flange, and a conductive nut, which rests on the other flange.

7. The surgical shears of claim 1, in which the shear members have cooperating blades, and in which the first and second electrical conductors supported on the first shear member are separated but close spaced and have tabs that extend respectively into separate tubular insulating bushings in two terminal-receiving bores into which terminals may be inserted to make good electrical contact with the respective tabs positioned on the first shear member so that electrical connections are kept as much out of the way of the hand of the surgeon and the blades as possible.

8. The surgical shears of claim 7, having a third terminal inserted and fixed into a third terminal-receiving bore in the first shear member, and making good electrical contact with the first shear member and hence with the shearing surface of the second shear member.

9. The surgical shears of claim 8, in which the terminal-receiving bores in the first shear member have parallel axes and are sufficiently closely spaced together to afford a convenient plug connection from all three electrodes through a common cable, to a power generator.

10. Surgical shears including high frequency electrodes for selectively cauterizing areas being cut by the shears comprising:

first and second electrically conductive shear members each having shearing surfaces and adjacent cutting edges and having an electrically insulating coating applied to surfaces other than the shearing surfaces;

mechanical fastening means for relatively rotatable connecting together and allowing relative scissor like motion between the first and second shear members so that in operative positions at least part of the shearing surfaces are opposed to one another and will be mechanically and electrically in contact with one another during use;

an electrode supported on each of the shear members in position to contact tissue when being cut by the shears, said electrode being insulated from the conductive portion of the respective first and second members by the electrically insulating coating;

a first electrical conductor supported on and insulated from the first shear member, connected to the electrode on the first shear member and providing terminal means for the connection to a power supply;

a third electrical conductor supported on and insulated from the second shear member and connected to the electrode on the second shear member and connected to electrical connection means passing through the mechanical fastening means, and;

a second electrical conductor mechanically supported on and electrically insulated from the first shear member and insulated from the first electrical conductor and the shearing surface by the insulating coating connected between a terminal means for connection to a power supply and the electrical connection means passing through the mechanical fastener means completing electrical connection to the electrode on the second shear means;

in which the first and second conductors are connectible to one terminal of a power supply through switch means for selectably supplying high frequency power to a selected one, or both, or neither, of the electrodes on the shear members, and having a separate terminal connected to the base metal of the first shear member for connection to the other terminal of the power supply.

* * * * *